United States Patent [19]

Sipos

[11] Patent Number: 5,405,621

[45] Date of Patent: * Apr. 11, 1995

[54] COMPOSITIONS OF GASTRIC ACID-RESISTANT MICROSPHERES CONTAINING BUFFERED BILE ACIDS

[75] Inventor: Tibor Sipos, Lebanon, N.J.

[73] Assignee: Digestive Care Inc., Lebanon, N.J.

[*] Notice: The portion of the term of this patent subsequent to Nov. 16, 2010 has been disclaimed.

[21] Appl. No.: 139,263

[22] Filed: Nov. 10, 1993

Related U.S. Application Data

[63] Continuation-in-part of Ser. No. 901,749, Jun. 19, 1992, Pat. No. 5,262,172.

[51] Int. Cl.$^6$ .................... A61K 9/54; A61K 9/58; A61K 9/62; A61K 9/16
[52] U.S. Cl. .................... 424/490; 424/494; 424/495; 424/497; 424/461; 424/462; 424/458; 424/474; 424/480; 424/482; 424/715; 424/717; 424/456; 514/867; 514/877; 514/893; 427/212; 427/213; 264/7; 264/13; 264/15
[58] Field of Search .................... 424/490, 461–462, 424/469–470, 480, 482, 494, 497–498, 715, 717; 514/819, 838, 867, 877, 893

[56] References Cited

U.S. PATENT DOCUMENTS

| | | | |
|---|---|---|---|
| Re. 30,910 | 4/1982 | Wiegand | 424/238 |
| 3,004,893 | 10/1961 | Martin | 167/73 |
| 4,079,125 | 3/1978 | Sipos | 424/32 |
| 4,280,971 | 7/1981 | Wischniewski et al. | 264/15 |
| 4,828,843 | 5/1989 | Pich et al. | 424/480 |

FOREIGN PATENT DOCUMENTS 1296944 11/1972 United Kingdom .
1362365 8/1974 United Kingdom .

*Primary Examiner*—Edward J. Webman

[57] ABSTRACT

Disclosed are gastric acid-resistant polymer-coated buffered-bile acid compositions, process for their preparations and methods of treating digestive disorders, impaired liver function, autoimmune diseases of the liver and biliary tract, preventing colon cancer, cholestasis associated with cystic fibrosis, dissolving gallstones and regulating dietary cholesterol absorption by administering said compositions to a mammal in need of such treatment.

21 Claims, No Drawings

COMPOSITIONS OF GASTRIC ACID-RESISTANT MICROSPHERES CONTAINING BUFFERED BILE ACIDS

This application is a continuation-in-part of application Ser. No. 07/90 1749, filed Jun. 19, 1992 issued as U.S. Pat. No. 5,262,172.

BACKGROUND OF THE INVENTION

1. Field of the Invention

This invention relates to buffer-stabilized bile acid compositions for ingestion by a mammal, a process for preparing said compositions, and a method for treating digestive disorders, impaired liver function, autoimmune diseases of the liver and biliary tract, preventing colon cancer, cholestasis associated with cystic fibrosis, dissolving gallstones and regulating dietary cholesterol absorption by administering said compositions to a mammal in need of such treatment.

2. Reported Developments

It is known in the prior art that ursodeoxycholic acid (hereinafter sometimes referred to as UDCA) administered to mammals can remedy UDCA deficiency caused by various diseased conditions of the liver, such as gallstones, liver toxicity due to toxic metabolites, alcohol induced hang-over, drug related toxicity, colon cancer following gallbladder surgery, and deficiency associated with poor digestion of fats and lipids in the intestine. UDCA requires the presence of certain conditions in order for it to be safe and effective as will be described hereunder.

UDCA, conjugated-UDCA and other bile acids are produced by the patient's liver, stored in the gallbladder and released into the duodenum in response to a meal, the pH of which is close to neutral or slightly alkaline. Under these basic pH conditions UDCA is soluble as sodium-UDCA (Na-UDCA) and biologically active and digestion of the food by UDCA proceeds normally in the upper segment of the intestine. However, when UDCA is administered exogenously to the patient, the gastric conditions in the stomach, namely the presence of acid, will render the UDCA insoluble. The insoluble UDCA is biologically inactive. Therefore, orally administered buffer-stabilized UDCA must be protected against gastric inactivation so that it remains intact during its transit through the stomach into the duodenum.

Once the exogenously introduced buffer-stabilized UDCA reaches the duodenum, another requirement must be satisfied: the buffer-stabilized UDCA must be released from its protective environment and intimately mixed with the food transferred from the stomach to effect digestion.

U.S. Pat. No. 4,079,125, incorporated herein by reference, addresses these requirements in a composition containing pancreatic enzymes, which closely approximate the behavior of UDCA in the acidic environment of the stomach and in the neutral-to-basic environment of the upper intestine, and provides preparative methods for making the compositions. The compositions provided by said patent comprise: an enzyme concentrate formulated with a binder/disintegrant and is coated with a non-porous, pharmaceutically acceptable enteric coating polymer which is insoluble in the pH range of from about 1.5 to about 5 normally present in gastric fluids, and soluble at a pH of from about 6 to about 9, the normal pH range for mammalian intestinal fluids. The orally administered composition passes through the stomach while being protected against the acidic environment by its acid-insoluble coating which then disintegrates in the neutral to basic environment of the upper intestine releasing the enzymes from the composition. The process of making the compositions includes the provision of using a solvent and avoiding the presence of water in the blending step of the enzyme/binder/disintegrant, since it is believed that water deactivates some of the enzymes.

It is known that ursodeoxycholic acid is capable of augmenting liver function, dissolving gallstones and improving the nutritional state of patients having cystic fibrosis caused by hepatobiliary complications. (See for example: Ursodeoxycholic acid dissolution of gallstones in cystic fibrosis. Sahl, B., Howat, J., Webb, K., *Thorax*, 43:490-1 (1988); Effects of Ursodeoxycholic Acid Therapy for Liver Disease Associated with Cystic Fibrosis. Colombo, C., Setcheil, K. D., Podda, M., Crosignani, A., Roda A., Curcio, L., Ronchi, M. and Giunta, A., *The Journal of Pediatrics*, 117:482-489 (1990); Effects of Ursodeoxycholic Acid Treatment on Nutrition and Liver Function in Patients with Cystic Fibrosis and Longstanding Cholestasis. Cotting, J., Lentze, M. J. and Reichen, J., *Gut* 31:918-921 (1990). Also, UDCA has recently gained acceptance as an effective therapeutic modality to dissolve small to medium size cholesterol gallstones in gallstone afflicted patients. (See for example: The Effect of High and Low Doses of Ursodeoxycholic Acid on Gallstone Dissolution in Humans, Salen, G., Colalillo, A., Verga, D., Bagan, E., Tint, G. S. and Shefer, S., *Gastro.*, 78:1412-1418 (1980); Ursodeoxycholic Acid: A Clinical Trial of a Safe and Effective Agent for Dissolving Cholesterol Gallstones, Tint, G. S., Salen, G., Colalillo, A., Graber, D., Verga, D. Speck, J. and Shefer, S., *Annals of Internal Medicine*, 91:1007-1018 (1986); Clinical Perspective on the Treatment of Gallstones with Ursodeoxycholic Acid, Salen, G., *J. Clin. Gastroenterology*, 10 (Suppl. 2):S12-17 (1988); Nonsurgical Treatment of Gallstones, Salen, G. and Tint, G. S., *New England J. Med.*, 320:665-66 (1989); and Reducing Cholesterol Levels, A. H. Weigand, U.S. Pat. No. 3,859,437. The recommended dosage is 10 to 15 mg/kg of body weight. In some patients much higher dosages (for example, about 30 mg/kg of body weight) are required to achieve limited benefits. However, in some patients undesirable side effects (such as severe diarrhea) seriously limit the use of this drug. The reasons for this wide variation of dosage requirements for therapeutic effectiveness and associated side effects are not completely understood. One hypothesis is that the acidic form of UDCA is only partially neutralized in the upper intestine to its sodium salt form due to deficiencies in bicarbonate secretion in some of the patients. Many patients, such as patients with cystic fibrosis, pancreatitis or Billroth I & II and many elderly are deficient in bicarbonate secretion and lack neutralization capacity. These patients will only partially benefit from UDCA therapy. The insoluble acidic form of UDCA is poorly absorbed from the intestine, and a good portion of the administered dosage is excreted intact with feces. When a higher dosage of the acidic form of UDCA is administered to the patient, a large portion of it is neutralized in the distal parts of the intestine which in turn induces diarrhea, a highly undesirable side effect. Also, if the acidic form of UDCA is to be converted into its salt form in the duodenum, it will temporarily exhaust the buffering capacity of the duodenum and it will render the upper intestine partially acidic. The acidic pH impedes the function of the pancreatic enzymes and UDCA cannot emulsify fats and facilitate the hydrolysis of lipids. Furthermore, the many therapeutic benefits derived from the salt forms of UDCA cannot be realized. Accordingly, the salt forms of UDCA should be administered to patients in need of UDCA, since only the ionized, i.e. salt form of UDCA possess the desirable biological characteristics in the upper intestine, including the following: 1) is readily absorbed from the intestine; 2) inhibits cholecystokinin release by the intestinal mucosa, thus ameliorating pain and producing symptomatic relief; 3) enhances the flow of bile which cleanses the liver cells from accumulated toxic metabolites and thus reduces liver toxicity and autoimmune diseases of the liver and biliary tract; 4) prevents the binding and absorption of deoxycholic acid in the colon, thus prevents colon cancer development; 5) prevents the crystallization of cholesterol into gallstones; 6) emulsifies fats; and 7) facilitates the hydrolysis of fat globules. U.S. Pat. No. 3,859,437 recommends the administration of a "small but effective amount sufficient to effect a reduction in the cholesterol level of said human being, of the compound 3$\alpha$, 7$\beta$-dihydroxy-5$\beta$-cholanic acid (UDCA) and the non-toxic pharmaceutically acceptable salts thereof." However, administering the salt form of UDCA to patients has no advantage over the acidic form of UDCA and does not accomplish the desired result since the salt form of UDCA is converted back to the acidic form of UDCA by gastric acidity. Furthermore, the salt forms, i.e., sodium or potassium, of UDCA are extremely bitter-tasting, and in most patients cause esophageal reflux, nausea and vomiting. Because of these highly undesirable organoleptic and gastric side effects, the salt forms of UDCA have not gained therapeutic utility in the treatment of biliary diseases.

It has now been discovered that the problems associated with tablets and capsules containing UDCA may be overcome in a composition containing buffer-stabilized UDCA instead of the acidic form of UDCA. In accordance with the discovery, UDCA is first buffered, processed into microspheres, and then coated with an acid-resistant polymer coating. Such composition overcomes the herein-described problems: 1) the polymer coating protects the buffer-stabilized UDCA from gastric acidity and neutralization of the buffer by the gastric acid; and 2) once the microspheres pass through the stomach in the duodenum, the protective coating dissolves in the neutral-to-alkaline range of the upper intestine. The microspheres disintegrate and release the buffer-stabilized UDCA into the intestine within ten to thirty minutes. Once the buffer-stabilized UDCA is released from the microspheres, the buffer salts provide a basic environment in which the UDCA is rapidly neutralized to its soluble salt form. The composition also provides extra buffering capacity to neutralize the acid chyme.

It has also been discovered that the buffer-stabilized UDCA composition can be prepared into microtablets and microspheres in the presence of moisture without inactivation of the bile acid composition thereby resulting in products that do not crumble upon drying or disintegrate upon initiation of the polymer coating procedure. This discovery is contrary to the teaching of the aforementioned U.S. Pat. No. 4,079,125 which requires complete exclusion of water (anhydrous condition) during the process of preparing pancreatic enzyme-containing microtablets and microspheres. It was found that anhydrous conditions leads to products that are extremely friable, tend to crumble into pieces upon drying in a fluidized bed dryer or a conventional coating pan and disintegrate upon initiation of the polymer coating step. This results in large amounts of dust and agglomeration of the beads into multiplets during the process as well as improper doses of buffer-stabilized UDCA upon administration to the patient when quality control fails adequately to sort-out and discard said rejects. The bitter taste and associated gastric disadvantages of UDCA are also eliminated by the polymer coating which prevents solubilization of the product in the mouth and stomach of the patient.

Still further, it has been discovered that microspheres in the range of 10 to 40 mesh size can be prepared utilizing buffer-stabilized UDCA as seeds to build up the microspheres. Such small particle size microspheres are especially beneficial for treating cholestasis and bile acid deficiencies in cystic fibrosis children.

SUMMARY OF THE INVENTION

This invention will be described with particular reference to buffer-stabilized ursodeoxycholic acid containing an amount of buffering agent sufficient to provide neutralization capacity in the upper intestines of patients deficient in bicarbonate secretion. However, it is to be understood that other bile acids such as cholic acid, deoxycholic acid, chenodeoxycholic acid and their glycyl, taurine, methylglycyl and methyltaurine conjugates, including their isomers may be used as well.

In co-pending application Serial No. 07/901,749, there is described a microencapsulated, polymer-coated composition comprising bile acids as the active ingredients for the treatment of bile acid deficiency. The instant composition contains a mixture of buffered-bile acid in a 1 to 1 neutralization equivalent ratio, and in addition, 5% w/w to 40% w/w of a buffering agent to provide buffering capacity to neutralize the acid chyme that is present in the intestine and re-establish the normal digestive conditions in patients deficient of intestinal buffers. Recent findings indicate that buffer deficiency is more serious in certain patients than believed heretofore. For example: cystic fibrosis patients are deficient in bicarbonate secretion and their upper intestinal pH's are in the range of 4.5 to 6.5; some of the alcohol induced cholestatic liver diseased patients' duodenal pH's are also in the less than neutral range, i.e. pH 6.0 to 7.6. Even when the pancreas and the gallbladder are maximally stimulated with secretin and cholecystokinin hormones, the intestinal pH's seldom exceed pH 7.0 in cystic fibrosis and 7.6 in alcohol induced liver diseased patients.

Because it is difficult to predict the extent of bicarbonate deficiency in these patient populations without intubation and collection of intestinal juices, it is necessary to assure that adequate amount of buffer is administered with the exogenous bile acid compositions.

Furthermore, ursodeoxycholic acid is insoluble at low pH's. At pH 7.0 only 20% and at 7.5 only 50% of a given dose of USDA is solvated. The other portions of the dose is excreted with the feces.

Accordingly, the composition of the present invention incorporates 5 to 40% w/w of a buffering agent, based on the total weight of the compositions, to provide optimum conditions for maximal biological activity of the exogenously administered bile acids.

In accordance with one aspect of the invention, there is provided a microencapsulated, polymer-coated composition comprising a buffered-bile acid in a novel pharmaceutical dosage form. In another aspect, the invention provides a process for preparing a buffer-stabilized bile acid for use in said composition. In still another aspect, the invention provides a process for the preparation of gastric acid-resistant polymer-coated buffer-stabilized bile acid containing microspheres and microtablets. In its final aspect the invention provides a method for treating bile acid deficiencies associated with biliary diseases in mammals, such as cholestasis and gallstones, liver toxicity due to toxic metabolites and autoimmune diseases of the liver and biliary tract, alcohol induced hang-over, drug related toxicity, prevention of colon cancer, deficiency associated with poor digestion of fats and lipids in the intestines, and regulating dietary cholesterol absorption.

Preparation of Buffered UDCA Micropheres & Microtablets

Recognizing the above limitations of bile acids it has now been discovered that by micropulverizing the bile acids in the presence of a suitable buffer salt one can obtain ultrafine particles of the buffered-bile acids that will readily dissolve in the intestinal juices under physiological conditions. The micropulverized and buffered-bile acid is physically converted into microspheres of 10 to 40 mesh size by a process of granulation with suitable solvents and polymeric binders, extruded into segments of 0.2 to 0.5 mm and rounded into spherical particles. The microspheres are coated with a gastric acid impermeable polymer coating that protects the buffer-stabilized bile acid from gastric acidity during gastric transit and releasing the buffer-stabilized bile acid in the duodenum under neutral condition. Once the buffer-stabilized bile acid is released from the microspheres into the upper intestine it is instantly converted to the salt of bile acid in situ. With the delivery of the buffer stabilized-bile acid into the duodenum in its biologically active state, one can achieve hitherto unrealized benefits of the salt of bile acid over the insoluble and poorly absorbed acidic form of the bile acid.

As previously indicated, only the salts of bile acids are absorbed from the intestine, while the acidic form of bile acids is passed through the intestine intact, unless it is converted to the sodium salt by intestinal buffers. However, many patients, such as patients with cystic fibrosis, pancreatitis, Billroth I & II diseases and some elderly people, are deficient in bicarbonate secretion and lack neutralization capacity to convert the acidic form of the bile acid to the sodium salt of bile acid. These patients will only partially benefit from the insoluble acidic form of the bile acid therapy. The buffered-bile acid-containing composition of the present invention overcomes this problem by the buffer converting the bile acid into a salt of bile acid in situ. Additionally, the composition also provides extra buffering capacity to neutralize the acid chyme that is present in the intestine.

The buffered-bile acid composition is microencapsulated and coated with an acid resistant polymer coating, which protects the composition from gastric acid. The polymer-coated microcapsules are tasteless and the problem associated with the offensive bitter taste of the uncoated acidic form or the uncoated salts of bile acids is thereby alleviated.

The microcapsules uniformly disperse with the food in the stomach and deliver high levels of biologically active bile acid into the duodenum. Once in the duodenum, the polymer coating dissolves within about 10 to 30 minutes and the buffered-bile acid is released to be converted into the soluble salt of the bile acid in situ. The soluble and biologically active bile acid enhances digestion of fats and lipids. As a result, the natural digestive conditions in the intestine are re-established. Epigastric pain, cramps, bloating, flatulence and stool frequency associated with maldigestion of fatty foods are reduced.

Soluble salts of bile acids formed by the presence of a buffer are absorbed more efficiently and in a greater quantity from the intestine than the insoluble acidic form of bile acids, resulting in a more efficient stimulation of the liver enzymes to conjugate bile acids and enhance choleresis. The increased concentration of the bile acid and conjugated bile acid stimulates bile flow, enhances the displacement of toxic bile acid metabolites from the hepatocytes, decreases cholesterol secretion into bile, alters the cholesterol/phospholipid ratio of secreted bile and decreases the absorption of dietary biliary cholesterol from the intestine. The overall result is decreased biliary cholesterol saturation, increased bile flow, dissolution of already formed cholesterol gallstones and protection of the liver from accumulated toxic metabolites.

Compositions of Buffered-Bile Acids

The buffer-stabilized bile acid composition comprises a blend of ingredients and a coating therefor expressed in weight per weight percentages based on the total weight of the composition:

a) from about 60 to about 84% of a buffered-bile acid mixture in a 1 to 1 neutralization equivalent ratio in a micropulverized powder form;

b) from 5% to about 40% of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular range of 350 to 50,000, di-, tri-, and poly-lysine in the molecular range of 290 to 15,000, diethylamine and triethanolamine;

c) from about 0 to about 16% and preferably from about 0.9 to about 16% of a disintegrant selected from the group consisting of starch and modified starches, microcrystalline cellulose and propylene glycol alginate;

d) from about 2.0 to about 15% of an adhesive polymer selected from the group consisting of polyvinylpyrrolidone, hydroxypropyl cellulose, microcrystalline cellulose, cellulose acetate phthalate, and a 60:40 blend of methyl cellulose and hydroxypropyl methyl cellulose; and e) from about 8.0 to about 16% of a non-porous, pharmaceutically acceptable gastric acid-resistant polymer-coating which contains less than 2% talc and which is insoluble in the pH range of from about 1.5 to about 5 but is soluble in the pH range of from about 5.5 to about 9.

The Process of Making the Microsphere

In accordance with the present invention, the buffered-bile acid composition is prepared by a process comprising the steps of:

a) blending dry, micropulverized powdery ingredients selected from the group consisting of (i) from about 60 to about 84% w/w of a buffered-bile acid in a 1 to 1 neutralization equivalent ratio; (ii) 5% w/w to 40% w/w of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular range of 350 to 50,000, di-, tri-, and poly-lysine in the molecular range of 290 to 15,000, diethylamine and triethanolamine; (iii) of from about 0 to about 16% w/w and preferably from about 0.9 to about 16% w/w of a disintegrant selected from the group consisting of starch and modified starches, microcrystalline cellulose and propylene glycol alginate; and (iv) from about 2.0% to about 15% w/w of an adhesive polymer selected from the group consisting of polyvinylpyrrolidone, hydroxypropyl cellulose, microcrystalline cellulose, cellulose acetate phthalate, and a 60:40 blend of methyl cellulose and hydroxypropyl methyl cellulose;

b) wetting said blended ingredients with a liquid to cause the blend to stick together, wherein said liquid is selected from the group consisting of: 1%–25% w/w ethanol/75%–99% w/w 2-propanol/0.2%–2% w/w water; 98%–99% w/w 2-propanol/0.2%– 2% w/w water; 1%–25% w/w methanol/0.2%–2% w/w water/75%–98% w/w 2 propanol/1%–5% w/w ethylacetate;

c) extruding the liquid-wetted blend through a 10 to 18 mesh S/S screen;

d) converting the extruded segment to a uniform diameter particle size;

e) compacting the uniform particles to spherical particles;

f) drying the spherical particles;

g) separating the spherical particles if not of uniform size according to desired sizes using U.S. Standard sieve screens;

h) coating the particles with a gastric acid-resistant polymer that protects the microspheres in the acidic pH's (pH<6) and dissolves under neutral or slightly basic conditions; and i) drying the polymer-coated spherical particles.

DETAILED DESCRIPTION OF THE INVENTION

In preparing the buffer-bile acid containing microspheres of the present invention utilizing the extrusion, uni-sizer and marumerization process (later described) moisture must be included in the liquid or solvent-adhesive composition to render the adhesive polymer sticky enough to bind the buffered-bile acid containing micropulverized fluffy powder into a pliable, solid mass. This prevents the crumbling of the microspheres during the drying and coating process as well as allows the preparation of much smaller particle size microspheres, i.e. in the range of 10 to 80 mesh. Accordingly, it was found that the moisture level during the preparation of the composition should be in the range of from about 0.2% w/w to about 2.5% w/w, preferably, in the range of 0.2% w/w to 1.5% w/w, and most preferably in the range of 0.2% w/w to 1.0% w/w. When the compositions contained such amounts of moisture, the microspheres were found to be stable on aging and the integrity of the microsphere was preserved.

Further reference is now made to the process of preparing compositions of the present invention.

The process of manufacturing the microspheres comprises the following steps:

a) The dry, micropulverized powdery ingredients are blended together in a conventional blender.

b) The blend is then wetted with a suitable liquid, hereinbefore described, that causes the dry blend to stick together. The stickiness of the blend can be tested by compressing a handful of the blend in the palm of the hand. If the composition is compressible and sticks together, but readily crumbles when squeezed between the fingers, sufficient liquid has been added to the composition for processing in the subsequent granulation step.

c) The blend is extruded though a 10 to 18 mesh S/S screen using an oscillating/reciprocating extruder or a twin-screw extruder at a medium-to-high speed.

d) The extruded particles are classified in a so-called uni-sizer vessel that rotates at 15 to 45 rpm for about 5 to 10 minutes. The particles in this vessel are converted to a uniform diameter particle size.

e) The uniform particles are then compacted in a marumerizer, which is essentially a cylindrical vessel with a rotating disk at the bottom thereof, for about 15 to 90 seconds. An alternative method of compacting the microspheres can also be accomplished in a rotating conventional coating pan. In this case, the particles are tumbled in the pan for about 15 to 30 minutes, with occasionally wetting the particles with a fine mist of a liquid selected from the group consisting off 1%–25% w/w ethanol/75%–99% w/w 2-propanol/0.2%–2% w/w water; 98%–99% w/w 2-propanol/0.2%–2% w/w water; 1%–25% w/w methanol/0.2%–2% w/w water/75%–98% w/w 2 propanol/1%–5% w/w ethylacetate.

f) The spherical particles are dried in an oven under a stream of dry air not exceeding 60° C. and 40% relative humidity.

g) The microspheres are separated according to the desired sizes using U.S. Standard sieve screens.

h) The microspheres having 10 to 20 and 30 to 40 mesh size are separately coated with an acid-resistant polymer in a fluidized bed coating equipment, or in a conventional coating pan according to standard operating procedures as described in the manufacturer's instruction manual.

i) The polymer-coated microspheres are then dried in an oven under a stream of warm and dry air, not exceeding 60° C. and 40% relative humidity until all the volatile substances (moisture and solvents) are removed.

The following examples will further serve to illustrate the compositions of the present invention wherein the compositions and the process of preparing them will be described with reference to microsphere forms; however, it is to be noted that the microtablet form of the composition and the process of making it is also intended to be covered by the present invention. The process of making the microtablet form of the composition is as follows:

a) blending dry, micropulverized powdery ingredients selected from the group consisting of (i) from about 60 to about 84% w/w of a buffered/bile acid in a 1 to 1 neutralization equivalent ratio; (ii) 5% w/w to 40% w/w of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular range of 350 to 50,000, di-, tri-, and poly-lysine in the molecular range of 290 to 15,000, diethylamine and triethanolamine; (iii) of from about 0 to about 16% w/w and preferably from about 0.9 to about 16% w/w of a disintegrant selected from the group consisting of starch and modified starches, microcrystalline cellulose and propylene glycol alginate; and (iv) from about 2.0% to about 15% w/w of an adhesive polymer selected from the group consisting of polyvinylpyrrolidone, hydroxypropyl cellulose, microcrystalline cellulose, cellulose acetate phthalate, and a 60:40 blend of methyl cellulose and hydroxypropyl methyl cellulose;

b) wetting said blended ingredients with a liquid to cause the blend to stick together, wherein said liquid is selected from the group consisting of: 1%–25% w/w ethanol/75%–99% w/w 2-propanol/0.2%–2% w/w water; 98%–99% w/w 2-propanol/0.2%–2% w/w water; 1%–25% w/w methanol/0.2%–2% w/w water/75%–98% w/w 2 propanol/1%–5% w/w ethylacetate;

c) granulating or extruding the liquid-wetted blend through a 10 to 18 mesh S/S screen;

d) drying the granulates or extruded particles;

e) admixing a lubricant, such as talc or magnesium stearate in the amount of 0.1 to 2%, based on the total weight of the composition, with the granulated or extruded particles;

f) compressing the particles into microtablets of an average diameter size of from about 1.0 to about 2.5 mm;

g) coating the microtablets with a gastric acid-resistant polymer that disintegrates under neutral or slightly basic conditions; and i) drying the polymer-coated microtablets.

| Ingredients | A (uncoated) % w/w | B (coated) % w/w |
|---|---|---|
| Example I: Formula Composition (microspheres) | | |
| Disintegrant | 6.0 | 5.2 |
| Buffered-UDCA (micronized) | 80.0 | 69.6 |
| Buffering agent (anhydrous) | 11.0 | 9.6 |
| Adhesive Polymer | 3.0 | 2.6 |
| Polymer coat/talc mixture | | 13.0 |
| Example II: Formula Composition (microspheres) | | |
| Disintegrant | 8.0 | 6.8 |
| Buffered-UDCA (micronized) | 67.0 | 56.8 |
| Buffering agent (anhydrous) | 20.0 | 16.9 |
| Adhesive Polymer | 5.0 | 4.2 |
| Polymer coat/talc mixture | | 15.3 |
| Example III: Formula Composition (microtablets) | | |
| Disintegrant | 3.0 | 2.7 |
| Buffered-UDCA (micronized) | 84.0 | 75.0 |
| Buffering agent (anhydrous) | 10.0 | 8.9 |
| Adhesive Polymer | 2.0 | 1.8 |
| Lubricant (stearic acid/Mg-stearate) | 1.0 | 0.9 |
| Polymer coat/talc mixture | | 10.7 |

Example IV: Formula Composition Containing Buffered-Bile Acid Starting Seed (polymer coated microspheres)

| Ingredients | % w/w |
|---|---|
| Buffered-UDCA starting seed (20–40 mesh) | 12.8 |
| Disintegrant | 2.3 |
| Buffering agent (anhydrous) | 10.1 |
| Buffered-UDCA (micronized) | 60.0 |
| Adhesive polymer mixture | 4.1 |
| Polymer coat/talc mixture | 10.7 |

The microspheres of Example IV were prepared by employing a conventional coating pan. The microspheres were built up to larger particle sizes by placing the buffered-UDCA containing 30 to 40 mesh starting seeds in the rotating coating pan, wetting the microspheres with the liquid/adhesive polymer-containing mixture, followed by slowly dusting the buffered UDCA/buffer/disintegrant composition over the tumbling and flowing buffered-UDCA containing seeds. The sequence of these steps is repeated until the seeds are built up into microspheres having diameters in the range of 10 to 20 mesh, preferably 14 to 16 mesh.

An alternate procedure for the preparation of the microspheres in Example IV was carried out in fluidized bed coating equipment (Glatt Mfg. Co.) using a Wurster column. The starting seeds were placed in the equipment and fluidization was started. The buffered-UDCA/disintegrant/buffer/adhesive polymer mixture was sprayed on the fluidized microspheres as a homogenous mixture at a rate that allowed the growth of the starting seeds to larger microspheres.

| Example V: Preparation of Buffered-UDCA Containing Starting Seeds | |
|---|---|
| Ingredients | % w/w |
| Buffered-UDCA (micronized) | 60.7 |
| Disintegrant | 16.0 |
| Buffering agent (anhydrous) | 14.6 |
| Adhesive polymer | 8.7 |

The process of making the buffered-UDCA containing starting seeds consisted of: 1) micropulverizing the buffered-UDCA blend in a centrifugal grinder or an impact pulverizer and blending the resultant buffered-UDCA, disintegrant and the buffering agent together for 10 minutes; 2) spraying the composition with the adhesive polymer mixture until the powdery blend agglomerated; and 3) extruding the liquid moistened composition through a 10 to 18 mesh S/S screen using an oscillating/reciprocating granulator or a twinscrew extruder. The subsequent processing steps were the same as outlined in Steps a through i in "The Process of Making the Microspheres" under Summary of the Invention. Reference is now made to the ingredients used in the above examples: Bile Acids: cholic acid, deoxycholic acid, chenodeoxycholic acid and their glycyl, taurine, methylglycyl and methyltaurine conjugates, including their isomers may be used as well. Disintegrant: Explotab (Mendell, Inc.) and microcrystalline cellulose. Buffering agents: from about 5% to about 40.0% w/w, sodium carbonate (anhydrous powder), sodium bicarbonate, potassium carbonate, ammonium carbonate, tromethamine, tris-carbonate (Di[tris(hydroxymethyl) aminomethane] carbonate), tris-glycine buffer (0.25 mole tris-base and 1.92 mole of glycine, pH 8.3), di-, tri-, and poly-arginine in the molecular range of 350 to 50,000, di-, tri-, and poly-lysine in the molecular range of 290 to 15,000, diethylamine and triethanolamine. Adhesive Polymeric Agents: Hydroxypropyl cellulose (Klucel HF, Hercules Co.), poly-vinyl pyrrolidone (Plasdone, GAF Co.), a 60:40 blend of methyl cellulose and hydroxypropyl methyl cellulose (Dow Chem. Co.), hydroxypropyl methyl cellulose (Grades 50 and 55, Eastman Kodak Co.), cellulose acetate phthalate (Eastman Kodak Co.) and propylene glycol alginate (Kelco Co.). Acid-resistant polymers to coat the microspheres and microtablets: hydroxypropyl methyl cellulose phthalate, Grades 50 and 55 (Eastman Kodak Co., or Shin-Etsu Chemical Co., Ltd.), AQUATERIC® aqueous enteric coating polymer dispersion (FMC Corp.), EUDRAGIT® acrylic based polymeric dispersion (Rohm Pharma GMBH, Germany), and cellulose acetate phthalate (Eastman Kodak Co.). The following example will further illustrate the composition of the acid-resistant polymer-coatings:

Example VI

| | % w/w |
|---|---|
| Cellulose acetate phthalate (CAP)* | 7.5 |
| Diethyl phthalate (DEP) | 2.0 |
| Isopropyl alcohol (IPA) | 45.0 |
| Ethylacetate (EtoAc) | 45.0 |
| Talc, USP | 0.5 | acid-impermeable polymer coat. When AQUATERIC® or EUDRAGIT® aqueous enteric coating polymer dispersion was employed in place of cellulose acetate phthalate (CAP), the microspheres were first sealed with a thin layer coat of the CAP (2–4% w/w of the microspheres) followed by coating with the AQUATERIC® or EUDRAGIT®. The advantage of using an aqueous based polymeric dispersion is to save on solvents that are evaporated during the solvent based coating step and cut down on environmental pollution.

Distribution of microspheres according to sizes is shown in Table I.

TABLE I
Distribution of the Microspheres According to Sizes

| Mesh Size | (mm) | Example IB Microspheres (%) | Example IIB Microspheres (%) |
|---|---|---|---|
| 10 | 2.00 | 6.2 | 3.3 |
| 14 | | 30.0 | 57.0 |
| 20 | 0.84 | 53.8 | 32.7 |
| 40 | 0.42 | 10.0 | 7.0 |

Method of Treating UDCA Deficiency

The composition of the present invention are orally administerable to patients having UDCA deficiency in an effective amount to treat such deficiency. The compositions are tasteless unlike the insoluble acidic form of UDCA administered per se which is associated with an offensive bitter taste. This advantage increases patient compliance in taking the medication. The microspheres are administerable admixed with food or they may be filled into hard gelatin capsules for administration in a conventional manner. In both methods of administration the microspheres pass through the stomach intact, being protected by their acid-resistant coating. While in the stomach, the microspheres uniformly disperse with the food therein and pass into the duodenum to deliver high levels of biologically active UDCA. In the duodenum the polymer coating dissolves within ten to thirty minutes and the buffer-stabilized UDCA is released.

The total amount of the composition required to be administered to a bile acid deficient patient will vary with the severity of the conditions, age and other physical characteristics of the patent. Physicians will prescribe the total amount, the dosage, the frequency of administration on a patient by patient basis. Generally, for bile acid deficient patients, from about 0.15 to about 0.75 grams of the composition are administered once or twice a day. Larger amount may, however, be required for certain conditions, such as for dissolving gallstones.

For ease of administration of the compositions it is preferred to use hard gelatin capsules containing about 0.25 to 0.4 grams microspheres or microtablets. Gelatin capsules which disintegrate in the acidic environment of the stomach are well-known and utilized in the prior art. Microtablets are of small size, having a diameter between about 1 to 5 mm and a thickness between 1 to 4 mm. The tablet is prepared by conventional tableting procedure. However, the compositions of the present invention in the form of very small particle sizes may be used per se. For example, young children, handicapped individuals with certain diseases and elderly patients are unable to swallow big gelatin capsules. Microspheres of very small size of the present invention could then be administered to these patients with liquid food, such as milk, apple sauce and semi-solid foods.

The advantages of the polymer-coated microspheres and microtablets over capsules and large tablets are well recognized in the administration of therapeutic medications. The microspheres and mini tablets disperse uniformly with the food in the stomach due to the smaller particle size of these particles and are more uniformly coated with the polymer-coating because of their spherical shape. They also release their UDCA content more readily than compressed large tablets or capsules. The microspheres are protected from gastric acidity by the acid-resistant polymer-coating during gastric transit. Once the microspheres reach the duodenum, the polymer-coating dissolves under neutral-to-slightly-alkaline conditions and the microspheres discharge their buffered-UDCA content in the upper intestine within minutes. The micropulverized UDCA is instantly neutralized by the provided buffer and converted to the Na-UDCA in situ. This release and instant neutralization of UDCA to its ionized form (Na-UDCA) results in an efficient emulsification of fats and lipids, digestion of the emulsified lipids by pancreatic lipase, liquefaction of mucus that obstructs the intestinal mucosa and acceleration of the enzymatic digestion of mucopolysaccharides. As a result of this synergetic interaction between bile salts and pancreatic enzymes, mucus is lysed, and the receptor sites on the intestinal villi are exposed to the outer environment. The unblocked receptors can bind essential metabolites and transport them through the intestinal membrane into portal circulation. The net result is the normalization of the intestinal digestive functions, enhanced absorption of the liberated metabolites and the amelioration of the dyspeptic symptoms associated with the upper gastrointestinal tract.

The invention, having been fully described, it will be apparent to one skilled in the art that changes and modifications can be made thereto without departing from the spirit and scope thereof.

What is claimed is:

1. A buffer-stabilized bile acid composition in the form of microspheres or microtablets for the treatment of bile acid deficiency of a mammal comprising, by weight per weight percentages based on the total weight of the composition:
  a) from about 60 to about 84% of a buffered-bile acid mixture in a 1 to 1 neutralization equivalent ratio in a micropulverized powder form wherein the buffer in said buffered-bile acid mixture is selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine;
  b) from about 5 to about 40% of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine;
  c) from about 0 to about 16% of a disintegrant selected from the group consisting of starch, modified starches, microcrystalline cellulose and propylene glycol alginate;
  d) from about 2 to about 15% of an adhesive polymer selected from the group consisting of hydroxypropyl cellulose, polyvinylpyrrolidone, cellulose acetate phthalate, methyl cellulose and propylene glycol alginate; and
  e) from about 8% to about 16% of an non-porous, gastric acid-resistant and pharmaceutically acceptable polymer-coating which contains less than 2% talc and which is insoluble in the pH range of from about 1.5 to about 5 but is soluble in the pH range of from about 5.5 to about 9.

2. The buffered bile acid composition of claim 1 wherein said bile acid is selected from the group consisting of cholic acid, deoxycholic acid, chenodeoxycholic acid and their glycyl, taurine, methylglycyl and methyltaurine conjugates, and their isomers.

3. A method for treating bile acid deficiency in mammals comprising:
  orally administering an effective amount of the composition of claim 1.

4. The method of claim 3 wherein said bile acid deficiency treatment is to eliminate in a mammal diseased states or conditions selected from the group consisting of: digestive disorders, impaired liver function, autoimmune diseases of the liver and biliary tract, preventing colon cancer, alcohol-induced hangover, drug related liver toxicity, deficiency associated with poor digestion of fats and lipids, cholestasis associated with cystic fibrosis, dissolving gallstones and regulating dietary cholesterol absorption.

5. The method of claim 3 wherein about 0.15 to 0.75 gms of the composition is administered to a bile acid deficient patient.

6. The method of claim 5 wherein said composition is administered in an acid disintegratable capsule containing from about 0.15 to about 0.4 grams of microspheres or microtablets.

7. The method of claim 5 wherein said composition is administered admixed with a liquid or a semi-solid food.

8. A process for preparing a buffer-stabilized bile acid composition for the treatment of bile acid deficient mammals comprising the steps of:
  a) blending dry, micropulverized powdery ingredients selected from the group consisting of (i) from about 60 to about 84% w/w of a buffered/bile acid in a 1 to 1 neutralization equivalent ratio wherein the buffer in said buffered-bile acid mixture is selected from the group consisting of sodium carbonate (anhydrous powder), sodium bicarbonate, potassium carbonate, ammonium carbonate, tromethamine, tris-carbonate (Di[tris(hydroxymethyl)-aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine; (ii) 5% w/w to 40% w/w of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)-aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine; (iii) of from about 0 to about 16% w/w of a disintegrant selected from the group consisting of starch, modified starches, microcrystalline cellulose and propylene glycol alginate; and (iv) from about 2.0% to about 15% w/w of an adhesive polymer selected from the group consisting of polyvinylpyrrolidone, hydroxypropyl cellulose, microcrystalline cellulose, cellulose acetate phthalate, methyl cellulose and hydroxypropyl methyl cellulose;
  b) wetting said blended ingredients with a liquid to cause the blend to stick together, wherein said liquid is selected from the group consisting of: 1%–25% w/w ethanol/75%–99% w/w 2-propanol/0.2%–2.5% w/w water; 98%–99% w/w 2-propanol/0.2%–2.5% w/w water; 1%–25% w/w methanol/0.2%–2.5% w/w water/75%–98% w/w 2 propanol/1%–5% w/w ethylacetate;
  c) extruding the liquid-wetted blend through a 10 to 18 mesh S/S screen;
  d) converting the extruded segment to a uniform diameter particle size of 10 to 40 mesh using a unisizer vessel;
  e) compacting the uniform particles to spherical particles in a marumerizer or in a coating pan;
  f) drying the spherical particles under drying conditions not exceeding 60° C. and 40% relative humidity;
  g) separating the spherical particles if not of uniform size according to desired sizes using U.S. Standard sieve screens;
  h) coating the particles with a gastric acid-resistant polymer that protects the microspheres in the acidic pH range of 1.5 to 5 and dissolves under neutral or basic conditions in the pH range of 5.5 to 9; and i) drying the polymer-coated spherical particles under drying conditions not exceeding 60° C. and 40% relative humidity.

9. The process of claim 8 wherein said bile acid is selected from the group consisting of cholic acid, deoxycholic acid, chenodeoxycholic acid and their glycyl, taurine, methylglycyl and methyltaurine conjugates, and their isomers.

10. The process of claim 8 wherein said composition is in the form of microspheres having a mesh size of about 10 to 40.

11. The process of claim 8 wherein said liquid for wetting the blended ingredient comprises from about 0.2% to about 2.0% moisture.

12. The process of claim 11 wherein said moisture content is from 0.2 to 1.5%.

13. The process of claim 11 wherein said moisture content is from 0.2 to 1.0%.

14. A method for treating bile acid deficiency in mammals comprising:
orally administering an effective amount of the composition prepared by the process of claim 8.

15. A process for preparing a buffered-bile acid composition for the treatment of bile acid deficient mammals comprising the steps of:
a) preparing a buffered-bile acid starting seed comprising: micropulverizing 60 to 84% w/w of a buffered-bile acid blend in a 1 to 1 neutralization equivalent ratio in a centrifugal grinder or an impact pulverizer wherein the buffer in said buffered-bile acid blend is selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine, and blending the resultant fine powder with 0 to 16% w/w of a disinterrant selected from the group consisting of starch, modified starches, microcrystalline cellulose and propylene glycol alginate and 5 to 40% of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine;
b) spraying said blend with a solution of from about 2 to about 15% w/w of an adhesive polymer selected from the group consisting of hydroxypropyl cellulose, polyvinylpyrrolidone, cellulose acetate phthalate, methyl cellulose and propylene glycol alginate in a liquid selected from the group consisting of 1%–25% w/w ethanol/75%–99% w/w 2-propanol/0.2%–2.5% w/w water; 98%–99% w/w 2-propanol/0.2%–2.15% w/w water; 1%–25% w/w methanol/0.2%–2.5% w/w water/75%–98% w/w 2 propanol/1%–5% w/w ethylacetate;
c) extruding the solvent moistened blend through a 10 to 18 mesh S/S screen;
d) converting the extruded segments to a uniform diameter particle size of 10 to 40 mesh using a uni-sizer vessel;
e) compacting the uniform particles to spherical particles in a marumerizer or in a coating pan;
f) drying the spherical particles under drying conditions not exceeding 60° C and 40% relative humidity;
g) separating the spherical particles having particle size of 10 to 20 and 39 to 49 mesh sizes using U.S. Standard sieve screens;
h) employing said 30 to 60 mesh particles as starting seeds for the preparation of larger microspheres in the 10 to 20 mesh size range by placing the 30 to 60 mesh starting seeds in a rotating coating pan, spraying the microspheres with from about 2 to about 15% w/w of an adhesive polymer selected from the group consisting of hydroxypropyl cellulose, polyvinylpyrrolidone, cellulose acetate phthalate, methyl cellulose and propylene glycol alginate in a liquid selected from the group consisting of 1%–25% w/w ethanol/75%–99% w/w 2-propanol/0.2%–2.5% w/w water; 98%–99% w/w 2-propanol/0.2%–2.5% w/w water: 1%–25% w/w methanol/0.2%–2.5% w/w water/75%–98% w/w 2 propanol/1%–5% w/w ethylacetate followed by dusting the buffered bile acid/disintegrant composition over the tumbling and flowing starting seeds until the desired particle sizes are obtained;
i) coating the particles with a gastric acid-resistant polymer that dissolves under neutral or basic conditions in the pH range of 5.5 to 9; and
j) drying the polymer-coated spherical particles under drying conditions not exceeding 60° C. and 40% relative humidity.

16. The process of claim 15 wherein the particle size range of said seeds is from about 10 to about 40 mesh.

17. The process of claim 15 wherein said starting seed is selected from the group consisting of: buffered-ursodeoxycholic acid, buffered-glycyl ursodeoxycholic acid, buffered-tauroursodeoxycholic acid, buffered-N-methyl glycyl ursodeoxycholic acid, and buffered-N-methyl tauroursodeoxycholic acid.

18. The process of claim 17 wherein said buffer is selected from the group consisting of: sodium carbonate (anhydrous powder), sodium bicarbonate, potassium carbonate, ammonium carbonate, tromethamine, tris-carbonate (Di[tris(hydroxymethyl)-aminomethane] carbonate), tris-glycine buffer (0.25 mole tris-base and 1.92 mole of glycine, pH 8.3), di-, tri-, and poly-arginine in the molecular range of 350 to 50,000, di-, tri-, and poly-lysine in the molecular range of 290 to 15,000, diethylamine and triethanolamine.

19. A method for treating bile acid deficiency in mammals comprising:
orally administering an effective amount of the composition prepared by the process of claim 15.

20. A process for preparing a buffered-bile acid composition in the form of microtablets for the treatment of bile acid deficient mammals comprising the steps of
a) blending dry, micropulverized powdery ingredients selected from the group consisting of (i) from about 60 to about 84% w/w of a buffered/bile acid in a 1 to 1 neutralization equivalent ratio in a micropulverized powder form wherein the buffer in said buffered-bile acid mixture is selected from the group consisting of sodium carbonate (anhydrous powder), sodium bicarbonate, potassium carbonate, ammonium carbonate, tromethamine, tris-carbonate (Di[tris(hydroxymethyl)-aminomethane] carbonate), tris-glycine buffer (0.25 mole tris-base and 1.92 mole of glycine, pH 8.3), di-, tri-, and poly-arginine in the molecular weight range of 350 to 50,000, di-, tri-, and poly-lysine in the molecular weight range of 290 to 15,000, diethylamine and triethanolamine; (ii) 5% w/w to 40% w/w of an additional buffering agent selected from the group consisting of sodium carbonate (anhydrous powder), sodium bicarbonate, potassium carbonate, ammonium carbonate, tromethamine, tris-carbonate (Di[tris(hydroxymethyl)aminomethane] carbonate), tris-glycine buffer (0.25 mole tris-base and 1.92 mole of glycine, pH 8.3), di-, tri-, and poly-arginine in the molecular range of 350 to 50,000, di-, tri-, and poly-lysine in the molecular range of 290 to 15,000, diethylamine and triethanolamine; (iii) of from about 0 to about 16% w/w of a disintegrant selected from the group consisting of starch, modified starches, microcrystalline cellulose and propylene glycol alginate; and (iv) from about 2.0% to about 15% w/w of an adhesive polymer selected from the group consisting of polyvinylpyrrolidone, hydroxypropyl cellulose, microcrystalline cellulose, cellulose acetate phthalate, methyl cellulose and hydroxypropyl methyl cellulose;

b) wetting said blended ingredients with a liquid to cause the blend to stick together, wherein said liquid is selected from the group consisting of: 1%–25% w/w ethanol/75%–99% w/w 2-propanol/0.2%–2.5% w/w water; 98%–99% w/w 2-propanol/0.2%–2.5% w/w water; 1%–25% w/w methanol/0.2%–2.5% w/w water/75%–98% w/w 2 propanol/1%–5% w/w ethylacetate;

c) granulating or extruding the liquid-wetted blend through a 10 to 18 mesh S/S screen;

d) drying the granulates or extruded particles under drying conditions not exceeding 60° C. and 40% relative humidity;

e) admixing a lubricant comprising talc or magnesium stearate in the amount of 0.1 to 2%, based on the total weight of the composition, with the granulated or extruded particles;

f) compressing the particles into microtablets of an average diameter size of from about 1.0 to about 2.5 mm;

g) coating the microtablets with a gastric acid-resistant polymer that disintegrates under neutral or basic conditions in the pH range of 5.5 to 9; and i) drying the polymer-coated microtablets under drying conditions not exceeding 60° C. and 40% relative humidity.

21. A method for treating bile acid deficiency in mammals comprising:
orally administering an effective amount of the composition prepared by the process of claim 20.

* * * * *